(12) United States Patent
Karlsson et al.

(10) Patent No.: US 8,075,517 B2
(45) Date of Patent: Dec. 13, 2011

(54) MEDICAMENT DELIVERY DEVICE

(75) Inventors: Sebastian Karlsson, Sundbyberg (SE); Gunnar Elmén, Huddinge (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 12/996,232

(22) PCT Filed: May 29, 2009

(86) PCT No.: PCT/EP2009/056672
§ 371 (c)(1),
(2), (4) Date: Dec. 6, 2010

(87) PCT Pub. No.: WO2009/150071
PCT Pub. Date: Dec. 17, 2009

(65) Prior Publication Data
US 2011/0077589 A1 Mar. 31, 2011

(30) Foreign Application Priority Data
Jun. 11, 2008 (SE) ...................................... 0801367

(51) Int. Cl.
*A61M 5/31* (2006.01)
*A61M 5/315* (2006.01)

(52) U.S. Cl. ........... 604/82; 604/134; 604/191; 604/218

(58) Field of Classification Search .................... 604/68, 604/70, 82–92, 165.02, 134–137, 181, 183, 604/187, 191, 218
See application file for complete search history.

(56) References Cited

U.S. PATENT DOCUMENTS

| | | | | |
|---|---|---|---|---|
| 4,394,863 A * | 7/1983 | Bartner | ........................... | 604/90 |
| 5,042,977 A * | 8/1991 | Bechtold et al. | .............. | 604/134 |
| 5,300,030 A * | 4/1994 | Crossman et al. | ............ | 604/136 |
| 5,620,421 A * | 4/1997 | Schmitz | ........................ | 604/135 |
| 6,371,939 B2 * | 4/2002 | Bergens et al. | ............... | 604/156 |
| 6,953,445 B2 * | 10/2005 | Wilmot et al. | .................. | 604/89 |
| 7,118,553 B2 * | 10/2006 | Scherer | ......................... | 604/136 |
| 7,291,132 B2 * | 11/2007 | DeRuntz et al. | ............. | 604/207 |
| 7,297,136 B2 * | 11/2007 | Wyrick | ......................... | 604/117 |
| 7,329,239 B2 * | 2/2008 | Safabash et al. | ............. | 604/136 |
| 7,381,201 B2 * | 6/2008 | Gilbert et al. | ................. | 604/181 |
| 7,500,963 B2 * | 3/2009 | Westbye et al. | .............. | 604/192 |
| 7,635,350 B2 * | 12/2009 | Scherer | ......................... | 604/136 |
| 7,674,246 B2 * | 3/2010 | Gillespie et al. | ............. | 604/181 |
| 7,736,333 B2 * | 6/2010 | Gillespie, III | ................ | 604/110 |
| 7,758,548 B2 * | 7/2010 | Gillespie et al. | ............. | 604/134 |

(Continued)

*Primary Examiner* — Nicholas D Lucchesi
*Assistant Examiner* — Quynh-Nhu H Vu
(74) *Attorney, Agent, or Firm* — Potomac Patent Group PLLC

(57) ABSTRACT

The present invention relates to medicament delivery device comprising a generally tubular distal housing part (19); a generally tubular medicament container holder (16); a medicament container (18); a plunger rod (32); resilient force; an actuation means (34) comprising flexible locking means and an activation button; a release means (40); and a resilient means (60) characterized in that said plunger rod comprises a number of stop engagements (38) arranged on its outer circumferential surface and arranged to co-act with corresponding stop engagements (37) on the flexible locking means, such that when said activation button is proximally depressed said stop engagement (37) on said flexible locking means come out of contact from one stop engagement (38) of the plunger rod; and such that when said activation button (48) is released, said resilient means (60) forces the activation button and thereby the flexible locking means to move distally such that said stop engagements (37) on said flexible locking means come into contact with another stop engagement (38) of the plunger rod.

11 Claims, 3 Drawing Sheets

U.S. PATENT DOCUMENTS

| | | | |
|---|---|---|---|
| 7,901,377 B1* | 3/2011 | Harrison et al. | 604/156 |
| 7,938,802 B2* | 5/2011 | Bicknell et al. | 604/135 |
| 7,955,303 B2* | 6/2011 | Burren et al. | 604/136 |
| 2001/0039394 A1* | 11/2001 | Weston | 604/72 |
| 2002/0120235 A1* | 8/2002 | Enggaard | 604/135 |
| 2002/0188251 A1* | 12/2002 | Staylor et al. | 604/70 |
| 2004/0127858 A1* | 7/2004 | Bendek et al. | 604/208 |
| 2005/0277886 A1* | 12/2005 | Hommann et al. | 604/136 |
| 2006/0178630 A1* | 8/2006 | Bostrom et al. | 604/135 |
| 2006/0270985 A1* | 11/2006 | Hommann et al. | 604/136 |
| 2008/0147006 A1* | 6/2008 | Brunnberg et al. | 604/136 |
| 2008/0154200 A1* | 6/2008 | Lesch | 604/135 |
| 2009/0137948 A1* | 5/2009 | Marshall et al. | 604/68 |
| 2009/0137949 A1* | 5/2009 | Landau et al. | 604/70 |
| 2009/0227955 A1* | 9/2009 | Hirschel et al. | 604/187 |
| 2009/0259181 A1* | 10/2009 | Moser | 604/135 |
| 2009/0318865 A1* | 12/2009 | Moller et al. | 604/135 |
| 2010/0094253 A1* | 4/2010 | Boyd et al. | 604/506 |
| 2010/0114025 A1* | 5/2010 | Moller | 604/135 |
| 2010/0249705 A1* | 9/2010 | Kronestedt | 604/134 |
| 2011/0166521 A1* | 7/2011 | Marshall et al. | 604/135 |

* cited by examiner

MEDICAMENT DELIVERY DEVICE

TECHNICAL AREA

The present invention relates to a medicament delivery device and in particular an injector for injecting medicament into the body of a patient.

TECHNICAL BACKGROUND

Medicament delivery devices such as injectors have become widespread on the market, and in particular injectors primarily intended for self-administration of medicament. In that context, the injectors should be easy and almost intuitive to handle and use, and therefore a number of automatic or semi-automatic features are built in.

One example of such an injector is disclosed in patent application No. EP 1 743 666. The injector is arranged with a number of automatic features where the most important is the auto-injection feature. This is solved according to the document in that a plunger rod, which can act on a container for expelling medicament, is arranged with an annular groove. Flexible tongues are placed in the groove for locking the position of the plunger rod. In turn, the flexible tongues are held in place by a locking ring surrounding the tongues. When the injection is performed the locking ring is moved axially somewhat, and also the tongues, whereby the locking ring releases the tongues, which in turn causes the tongues to flex out of the groove of the plunger rod. The plunger rod is now free to move and is pushed towards the medicament container due to a drive spring and the injection is performed until the stopper inside the medicament container reaches its foremost position, in which the dose delivery is completed.

For some medicament rather large dose quantities are needed to be injected, often also with rather large needles. These large doses can be rather painful for the patient when they are injected into the tissue in one continuous movement, as with the injector described in EP 1 743 666. There are also some medicament types that as such cause pain when in contact with the tissue. When self-administering, there could thus be a risk that the patient withdraws the injector due to the pain or discomfort, before the whole dose is delivered. It would thus be desirable to temporarily stop the injection a number of times and allow the injected part of the dose to spread into the tissue before continuing the injection.

Document U.S. Pat. No. 5,679,111 discloses an injection device comprising an auto injection mechanism comprising a plunger rod operated by an injection spring for expelling a preset dose of medicament and a user controlled releasable plunger rod locking mechanism. The latter comprises a longitudinal groove with a wedge-shaped cross-section and a locking lug with cooperating cross-section. The locking lug is urged into the groove for locking the movement of the plunger rod. The locking lug can be moved out of contact with the groove by a user-operated handle whereby the plunger rod is moved, until the handle is again released or that the plunger rod comes to a dose stop. Thus the user is capable of controlling the injection sequence via the handle/lug in and out of frictional contact with the groove of the plunger rod.

A drawback with the device according to '111 is the use of frictional forces for holding/locking said plunger rod. A person skilled in the art is well aware of that the force from an injection spring needs to be rather high, in particular at the start of the injection sequence for overcoming the initial forces for moving a stopper inside the medicament container. It is thus not certain that the friction forces are capable of withstanding the forces from the injection spring.

Also, when the plunger rod is moving with a certain speed during injection, it might be impossible to stop the movement by mere friction. It is thus doubtful as to whether frictional locking mechanisms are capable of providing the user with real possibility of temporarily stopping an injection sequence as mentioned above.

There is thus room for improvements regarding the possibilities for a user to control an injection sequence.

BRIEF DESCRIPTION OF THE INVENTION

The aim of the present invention is to remedy the drawbacks with the state of the art devices and to allow a dose of medicament to be delivered in sequence in smaller parts with temporary stops of the delivery.

This aim is obtained by the delivery device according to the features of the independent patent claim. Preferable embodiments of the present invention form the subject of the dependent patent claims.

According to a main aspect of the invention it is characterised by a medicament delivery device comprising a generally tubular distal housing part; a generally tubular medicament container holder having opposite distal and proximal ends, wherein its distal end is releasably connected to said distal housing part and wherein its proximal end is releasably connected to a delivery member; a medicament container having at least one slidable stopper, wherein the container is arranged within the container holder; a plunger rod having opposite proximal and distal ends and being arranged within said distal housing part, wherein the proximal end of the plunger rod is abutting the at least one stopper; resilient force means operably connected to said plunger rod for driving said plunger rod and thereby said at least one stopper towards the proximal end of the device, an actuation means comprising flexible locking means releasably connected to said plunger rod for holding said plunger rod and thereby said resilient force means in a pre-tensioned state, and an activation button distally protruding from said distal housing part; a release means being slidably displaceable around said flexible locking between a first position wherein said release means completely surrounds said flexible locking means and a second position wherein said release means partially surrounds said flexible locking means after said release means has been distally displaced by said container holder when said container holder has been displaced into said distal housing part; and wherein said flexible locking means are arranged to be released from said plunger rod only after said release means is moved from the first position to the second position and said activation button is proximally depressed, such that the flexible locking means comes completely out of contact with the release means; and a resilient means arranged surrounding said release means and arranged to act axially on said actuation means wherein said plunger rod comprises a number of stop engagements arranged on its outer circumferential surface and arranged to co-act with corresponding stop engagements on the flexible locking means, such that when said activation button is proximally depressed said stop engagement on said flexible locking means come out of contact from one stop engagement of the plunger rod; and such that when said activation button is released, said resilient means forces the activation button and thereby the flexible locking means to move distally such that said stop engagements on said flexible locking means come into contact with another stop engagement of the plunger rod.

According to a further aspect of the invention, said flexible locking means are flexible tongues, said stop engagement means of the flexible locking means are inwardly directed protrusions, and said stop engagement means of the plunger rod are circumferential grooves.

According to another aspect of the invention, said medicament container is a multi chamber container comprising at least two substances.

According to yet an aspect of the invention, the distal housing part comprises mix engagement means arranged to cooperate with corresponding mix engagement means arranged on the distal end of the container holder, such that a distal displacement of the container holder in relation to the distal housing part causes a distal displacement of the container in relation to the plunger rod, whereby the plunger rod forces the stopper to be proximally displaced and thereby a mixing of the substances within the container is performed.

According to a further aspect of the invention, said mix engagement means are threads.

According to yet an aspect of the invention, the stop engagement means of the flexible locking means the stop engagement means of the plunger rod are circumferential produces audible indications as long as a continuous delivery is in progress.

The present invention has a number of advantages. The main advantage is that the manually operated actuation means is capable of releasing, but also locking, the plunger rod even after release. This means that the plunger rod can be locked in different positions during its travel, and thus during expelling of medicament.

This is a great advantage for some patients and some medicament types, in particular when the medicament doses prescribed are rather large, and/or painful to inject. The patient or user can then temporarily stop the delivery in order to rest, or to allow the injected medicament to spread in the tissue. The patient can then continue the delivery in steps.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
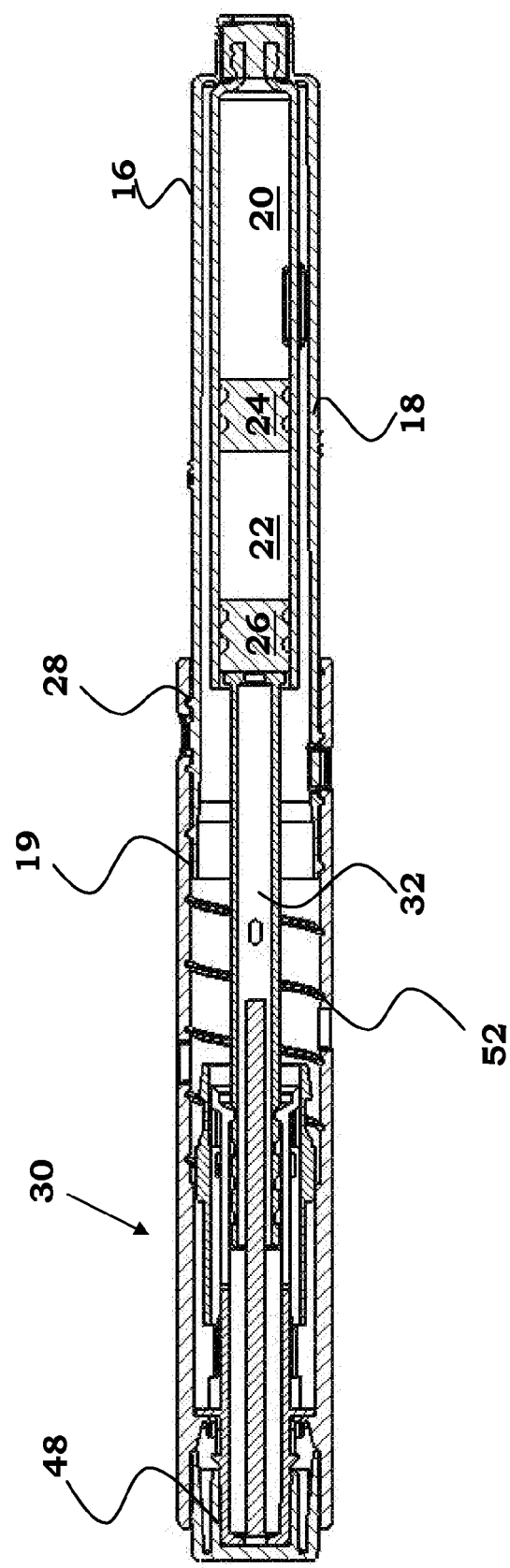
FIG. 1 is a cross-sectional view of one embodiment of the present invention.
Figure 2:
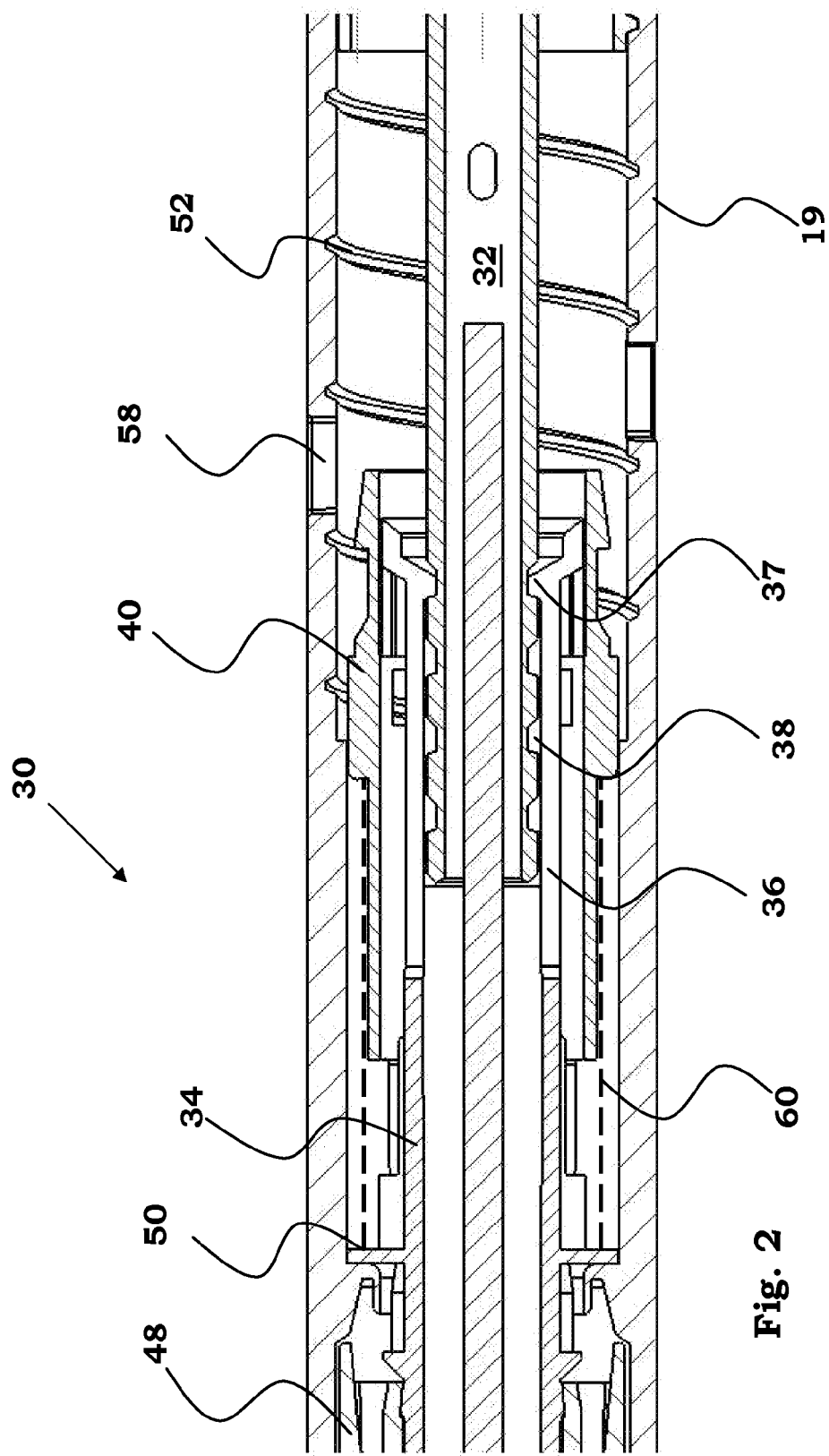
FIG. 2 is detailed view of a part of the embodiment of FIG. 1.
Figure 3:
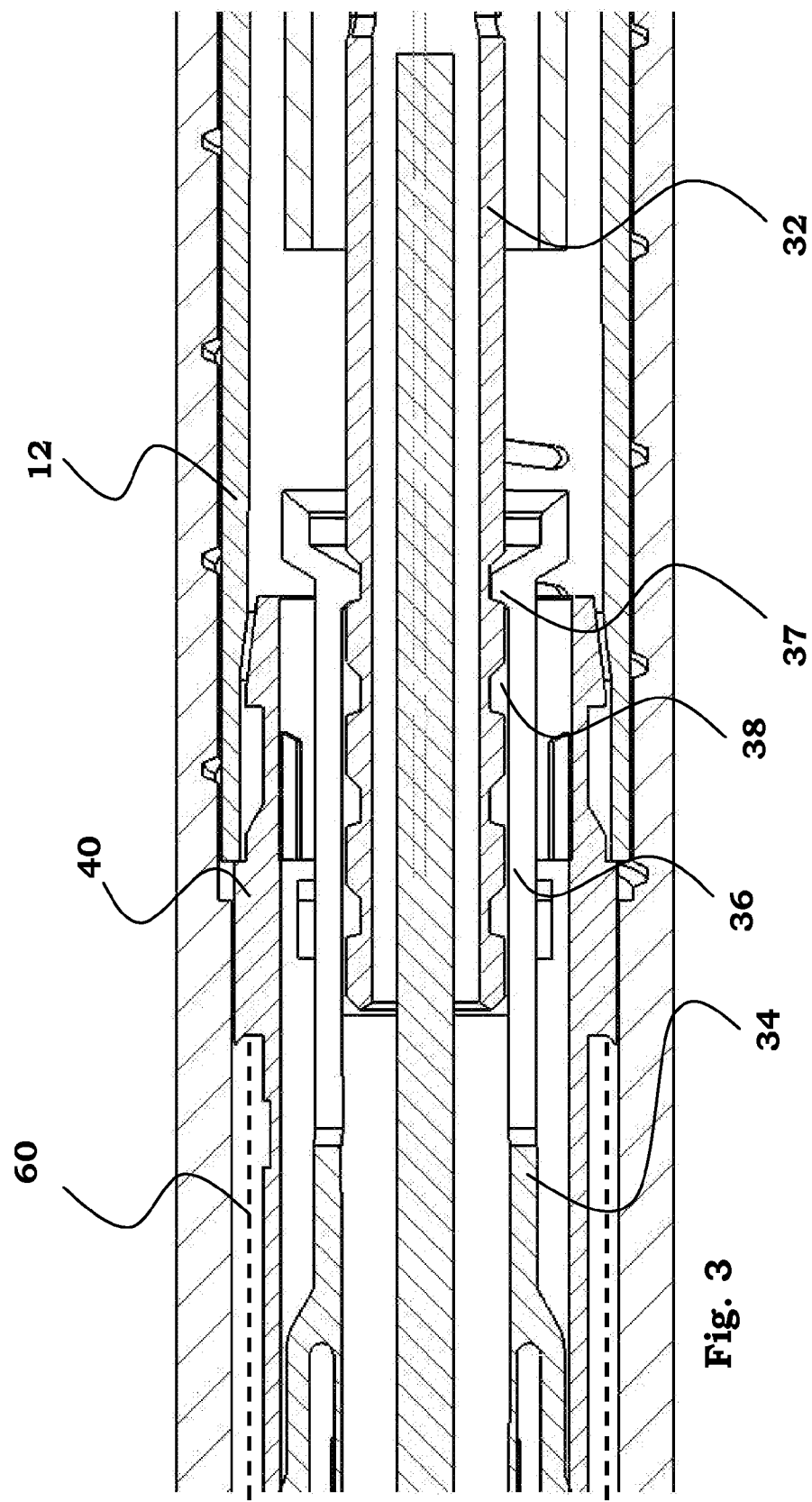
FIG. 3 is a further detailed view corresponding to FIG. 2.

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the device is located closest to the medicament delivery site of the patient.

The embodiment of a medicament delivery device shown in the figures comprises a generally tubular distal housing part 19; a generally tubular medicament container holder 16 having opposite distal and proximal ends, wherein its distal end is releasably connected to said distal housing part and wherein its proximal end is releasably connected to a delivery member; a medicament container 18 having at least one slidable stopper, wherein the container is arranged within the container holder; a plunger rod 32 having opposite proximal and distal ends and being arranged within said distal housing part, wherein the proximal end of the plunger rod is abutting the at least one stopper; resilient force means operably connected to said plunger rod for driving said plunger rod and thereby said at least one stopper towards the proximal end of the device, an actuation means 34 comprising flexible locking means 36 releasably connected to said plunger rod for holding said plunger rod and thereby said resilient force means in a pre-tensioned state, and an activation button 48 distally protruding from said distal housing part; a release means 40 being slidably displaceable around said flexible locking between a first position wherein said release means completely surrounds said flexible locking means and a second position wherein said release means partially surrounds said flexible locking means after said release means has been distally displaced by said container holder when said container holder has been displaced into said distal housing part; and wherein said flexible locking means are arranged to be released from said plunger rod only after said release means is moved from the first position to the second position and said activation button is proximally depressed, such that the flexible locking means comes completely out of contact with the release means; and a resilient means 60 arranged surrounding said release means and arranged to act axially on said actuation means wherein said plunger rod comprises a number of stop engagements 38 arranged on its outer circumferential surface and arranged to co-act with corresponding stop engagements 37 on the flexible locking means, such that when said activation button is proximally depressed said stop engagement 37 on said flexible locking means come out of contact from one stop engagement 38 of the plunger rod; and such that when said activation button 48 is released, said resilient means 60 forces the activation button and thereby the flexible locking means to move distally such that said stop engagements 37 on said flexible locking means come into contact with another stop engagement 38 of the plunger rod.

In the embodiment shown, the medicament container 18 is a so called multiple chamber container where one chamber 20 contains medicament in powder form and the other chamber 22 contains a diluent. The two chambers are sealed off by a first stopper 24. The end of the container is sealed off by a second stopper 26. Further, the outer surface of the medicament container holder 16 is arranged with mix engagement means 28 as e.g. threads.

The plunger rod 32 is partially surrounded by the actuation means 34. The proximal end of the actuation sleeve 34 is arranged with the flexible locking means 36 which are flexible tongues. Each tongue is arranged with the stop engagement means 37 which are inwardly directed protrusions. In the initial state, these stop engagement means 37 are positioned in corresponding stop engagement means 38 which is a first circumferential groove on the plunger rod where the groove acts as a stop ledge on which the protrusions 37 rest. Along the plunger rod, a number of circumferential grooves are arranged, the function of which will be described below. The tongues 36 and protrusions 37 are held in this initial position by the release means 40. Inside the plunger rod, the resilient force means which is e.g. a spring (not shown) is arranged compressed between a proximal wall part of the plunger rod and a distal wall part of the actuation means 34. The distal end of the actuation means 34 which is the activation button 48 protrudes distally though the distal end of the distal housing part. The actuation means is further arranged with a ledge 50 preventing the actuation means from moving in the distal direction. The inner surface of the distal housing part 29 is further arranged with mix engagement means 52 as e.g. threads having a corresponding pitch as the threads 28 of the container holder 16. The distal end of the resilient means 60 rests against the ledge 50 of the actuation means 34 and the proximal end of the resilient means rests against a ledge of the release means 40.

When the device is delivered to a user/patient, the medicament container is already placed within the medicament holder, the medicament holder is attached to the distal housing part, and the proximal end of the plunger rod is abutting the stopper arranged within the medicament container.

When the medicament container is a single chamber medicament container; the container holder 16 is somewhat distally displaced into the distal housing such that the distal end of the container holder comes in contact with the proximal end of the release means 40 and forces distally said release means compressing said resilient means 60, such that it is only partly in contact with the flexible tongues of the actuation means.

When the medicament container 18, FIG. 1, is a multiple chamber container; the container holder is distally displaced e.g. threaded into the distal housing part. Because the plunger rod is stationary and is abutting the second stopper 26, the second stopper 26 is forced against the plunger rod. Due to the incompressibility of the diluent in the chamber, the first stopper 24 is also moved, whereby passages of the container are freed between the first and the second chamber 20, 22 and a mixing is obtained. The user can now stop the distally displacement of the container holder. This may be indicated in a window 58 arranged on a surface on the proximal end of the distal housing part. A delivery member as e.g. a pen needle (not shown) is then attached to the proximal end of the container holder whereby a priming of the device is performed.

The device now is positioned at the intended delivery site e.g. an injection site, the delivery member which is e.g. a pen needle penetrates the skin, and the medicament is injected by proximally depressing the actuation button 48. This causes the actuation means 34 to move proximally, whereby the flexible tongues 36 flexes radially outwards causing the protrusions 37 to be moved out of the annular groove 38, which releases the plunger rod 32. The accumulated force in the pre-tensioned resilient force means forces the plunger rod to push the stoppers 24, 26 in the proximal direction whereby the expelling of a dose of medicament through the delivery member is initiated.

Moreover, if the patient/user feels pain or discomfort he/she can release the pressure on the actuation button 48. This causes the actuation means 34 to move distally due to the compression force of the resilient means, whereby the flexible tongues 36 are forced inwards toward the plunger rod due to the contact with the release means 40. Due to the sequence of annular grooves 38, the protrusions 37 of the tongues 36 will be positioned in one of the grooves 38, whereby the movement of the plunger rod 32 is stopped. The patient can now rest a while and let the delivered medicament to spread in the tissue. When the patient is ready to continue, he/she merely presses the actuation button 48 as described above and the delivery continues. This sequence with temporary stops may be performed a number of times until the last annular groove 38 has passed the protrusions 37. Of course, the patient does not have to stop but could let the device perform a continuous injection until the stoppers are in the foremost proximal position inside the medicament container. In this case, the protrusions 37 of the flexible tongues 36 will merely slide over the annular grooves 38, whereby an audible indication is obtained as long as a continuous delivery is performed. When this indication stops, this in turn is an indication that the delivery is completed.

After the delivery is completed and the delivery member has been withdrawn, the device is discarded. Further, additional features such as automatic penetration function, automatic needle shield function and the like can be used.

It is to be understood that the embodiment described above and shown in the drawings is to be regarded as a non-limiting example only and that it may be modified in many ways within the scope of the patent claims.

The invention claimed is:

1. A medicament delivery device, comprising:
a generally tubular distal housing part;
a generally tubular medicament container holder having opposite distal and proximal ends, wherein the distal end is releasably connected to the distal housing part, and the proximal end is releasably connected to a delivery member;
a medicament container having at least one slidable stopper, wherein the container is arranged within the container holder;
a plunger rod having opposite proximal and distal ends and arranged within the distal housing part, wherein the proximal end of the plunger rod abuts the at least one slidable stopper;
a resilient force mechanism operably connected to the plunger rod for driving the plunger rod and thereby the at least one slidable stopper toward a proximal end of the device;
an actuation mechanism, comprising a flexible locking device releasably connected to the plunger rod for holding the plunger rod and thereby the resilient force mechanism in a pre-tensioned state, and an activation button distally protruding from the distal housing part;
a release mechanism slidably displaceable around the flexible locking device between a first position, in which the release mechanism completely surrounds the flexible locking device, and a second position, in which the release mechanism partially surrounds the flexible locking device after the release mechanism is distally displaced by the container holder when the container holder is displaced into the distal housing part; wherein the flexible locking device is arranged to be released from the plunger rod only after the release mechanism is moved from the first position to the second position and the activation button is proximally depressed, such that the flexible locking device comes completely out of contact with the release mechanism; and
a resilient device arranged surrounding the release mechanism and to act axially on the actuation mechanism;
wherein the plunger rod comprises a number of stop engagements arranged on its outer circumferential surface to co-act with corresponding stop engagements arranged on the flexible locking device, such that when the activation button is proximally depressed, stop engagements on the flexible locking device come out of contact with a stop engagement on the plunger rod, and such that when the activation button is released, the resilient device forces the activation button and thereby the flexible locking device to move distally such that stop engagements on the flexible locking device come into contact with another stop engagement on the plunger rod.

2. The medicament delivery device of claim 1, wherein the flexible locking device includes flexible tongues, the stop engagements on the flexible locking device are inwardly directed protrusions, and the stop engagements on the plunger rod are circumferential grooves.

3. The medicament delivery device of claim 2, wherein the medicament container is a multi-chamber container and includes at least two substances.

4. The medicament delivery device of claim 3, wherein the distal housing part comprises a mix engagement device arranged to cooperate with a corresponding mix engagement device arranged on the distal end of the container holder, such that distal displacement of the container holder in relation to the distal housing part causes distal displacement of the container in relation to the plunger rod, whereby the plunger rod forces the stopper to be proximally displaced, thereby mixing the substances within the container.

5. The medicament delivery device of claim 4, wherein the mix devices include threads.

6. The medicament delivery device of claim 1, wherein the stop engagements on the flexible locking device and the stop engagements on the plunger rod are circumferential and produce an audible indication as long as a continuous medicament delivery is in progress.

7. A medicament delivery device, comprising:
- a generally tubular distal housing part;
- a generally tubular medicament container holder having opposite distal and proximal ends, wherein the distal end is releasably connected to the distal housing part, and the proximal end is releasably connected to a delivery member;
- a medicament container having at least one slidable stopper, wherein the container is arranged within the container holder;
- a plunger rod having opposite proximal and distal ends and arranged within the distal housing part, wherein the proximal end of the plunger rod abuts the at least one slidable stopper;
- a resilient force mechanism operably connected to the plunger rod for driving the plunger rod and thereby the at least one slidable stopper toward a proximal end of the device;
- an actuation mechanism, comprising a flexible locking device releasably connected to the plunger rod for holding the plunger rod and thereby the resilient force mechanism in a pre-tensioned state, and an activation button distally protruding from the distal housing part;
- a release mechanism slidably displaceable around the flexible locking device between a first position, in which the release mechanism completely surrounds the flexible locking device, and a second position, in which the release mechanism partially surrounds the flexible locking device after the release mechanism is distally displaced by the container holder when the container holder is displaced into the distal housing part; wherein the flexible locking device is arranged to be released from the plunger rod only after the release mechanism is moved from the first position to the second position and the activation button is proximally depressed, such that the flexible locking device comes completely out of contact with the release mechanism; and
- a resilient device arranged surrounding the release mechanism and to act axially on the actuation mechanism;
- wherein the plunger rod comprises a number of stop engagements arranged on its outer circumferential surface to co-act with corresponding stop engagements arranged on the flexible locking device, such that when the activation button is proximally depressed, stop engagements on the flexible locking device come out of contact with a stop engagement on the plunger rod, and such that when the activation button is released, the resilient device forces the activation button and thereby the flexible locking device to move distally such that stop engagements on the flexible locking device come into contact with another stop engagement on the plunger rod.

8. The medicament delivery device of claim 7, wherein the medicament container is a multi-chamber container and includes at least two substances.

9. The medicament delivery device of claim 8, wherein the distal housing part comprises a mix engagement device arranged to cooperate with a corresponding mix engagement device arranged on the distal end of the container holder, such that distal displacement of the container holder in relation to the distal housing part causes distal displacement of the container in relation to the plunger rod, whereby the plunger rod forces the stopper to be proximally displaced, thereby mixing the substances within the container.

10. The medicament delivery device of claim 9, wherein the mix devices include threads.

11. The medicament delivery device of claim 7, wherein the stop engagements on the flexible locking device and the stop engagements on the plunger rod are circumferential and produce an audible indication as long as a continuous medicament delivery is in progress.

* * * * *